United States Patent
Berger et al.

(10) Patent No.: US 9,055,923 B2
(45) Date of Patent: Jun. 16, 2015

(54) COMPUTED RADIOGRAPHY POSITIONING METHOD AND SYSTEM

(71) Applicants: Amir Berger, Kiryat Bialik (IL); Shmuel Yitzhaki, Yokneam (IL); Arkadi Kanovich, Haifa (IL)

(72) Inventors: Amir Berger, Kiryat Bialik (IL); Shmuel Yitzhaki, Yokneam (IL); Arkadi Kanovich, Haifa (IL)

(73) Assignee: Carestream Health, Inc., Rochester, NY (US)

( * ) Notice: Subject to any disclaimer, the term of this patent is extended or adjusted under 35 U.S.C. 154(b) by 125 days.

(21) Appl. No.: 13/776,867

(22) Filed: Feb. 26, 2013

(65) Prior Publication Data

US 2014/0112439 A1    Apr. 24, 2014

Related U.S. Application Data

(60) Provisional application No. 61/715,862, filed on Oct. 19, 2012.

(51) Int. Cl.
*A61B 6/00* (2006.01)
*A61B 6/14* (2006.01)
*A61B 6/08* (2006.01)

(52) U.S. Cl.
CPC ................. *A61B 6/587* (2013.01); *A61B 6/145* (2013.01); *A61B 6/4494* (2013.01); *A61B 6/08* (2013.01); *A61B 6/547* (2013.01)

(58) Field of Classification Search
CPC ...... A61B 6/587; A61B 6/145; A61B 6/4494; A61B 6/08; A61B 6/547
USPC ........... 378/19, 98.8, 162, 165, 168, 191, 205
See application file for complete search history.

(56) References Cited

U.S. PATENT DOCUMENTS

| | | | |
|---|---|---|---|
| 3,868,565 A | 2/1975 | Kuipers | |
| 4,054,881 A | 10/1977 | Raab | |
| 4,298,874 A | 11/1981 | Kuipers | |
| 4,314,251 A | 2/1982 | Raab | |
| 5,425,367 A | 6/1995 | Shapiro et al. | |
| 5,463,669 A * | 10/1995 | Kaplan | 378/205 |
| 7,006,838 B2 | 2/2006 | Diener et al. | |
| 7,211,785 B1 | 5/2007 | Berger et al. | |

(Continued)

FOREIGN PATENT DOCUMENTS

WO   2011/141763   11/2011

OTHER PUBLICATIONS

International Search Report for International Patent Application No. PCT/US2013/059856 mailed Jan. 8, 2014, 4 pages.

*Primary Examiner* — Irakli Kiknadze

(57) ABSTRACT

An apparatus for obtaining an intraoral x-ray image from a patient, the apparatus has an x-ray source and a radio-frequency transceiver coupled to the x-ray source and energizable to transmit an interrogation signal, wherein the transceiver is in signal communication with four or more antennae. An intraoral image detector forms an image upon exposure to radiation received from the x-ray source. A radio-frequency transponder is coupled to the image detector and is configured to respond to the interrogation signal by transmitting a wireless response signal. A control logic processor is in communication with the transceiver and provides an output signal indicative of the spatial position of the image detector according to response signals received from the transponder at the four or more antennae. An indicator responds to the output signal by indicating the relative position of the image detector.

15 Claims, 18 Drawing Sheets

(56) References Cited

U.S. PATENT DOCUMENTS

| | | |
|---|---|---|
| 7,319,396 B2 * | 1/2008 | Homanfar et al. ......... 340/572.1 |
| 7,567,651 B2 * | 7/2009 | Serceki et al. ................ 378/162 |
| 7,577,444 B2 | 8/2009 | Bird et al. |
| 7,677,799 B2 * | 3/2010 | Jensen et al. .................. 378/205 |
| 7,780,350 B2 | 8/2010 | Tranchant et al. |
| 2002/0150215 A1 | 10/2002 | Barnes et al. |
| 2006/0280293 A1 | 12/2006 | Hardesty |
| 2007/0001905 A1 | 1/2007 | Eronen |
| 2008/0002808 A1 | 1/2008 | De Godzinsky |
| 2009/0052618 A1 | 2/2009 | Homanfar et al. |
| 2009/0060145 A1 | 3/2009 | Tranchant et al. |

* cited by examiner

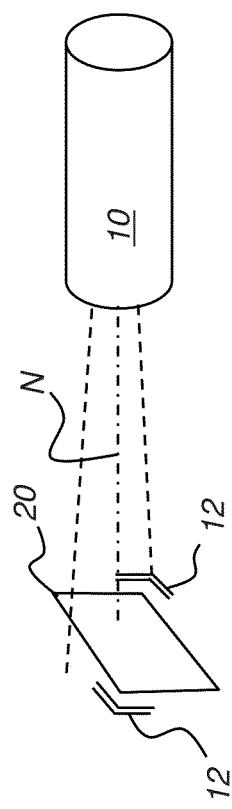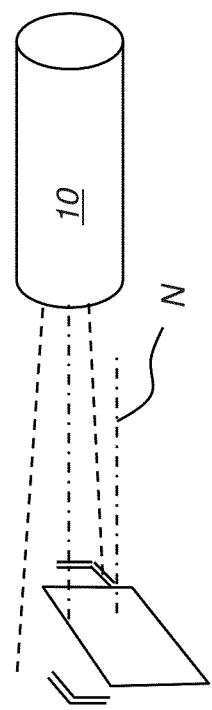

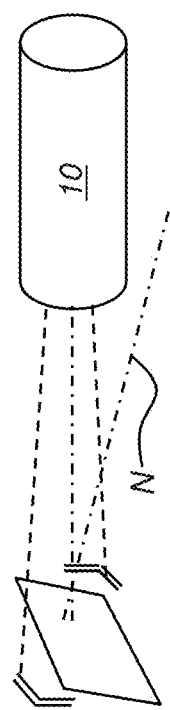

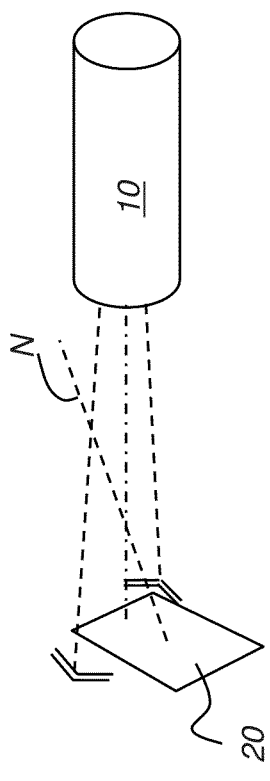
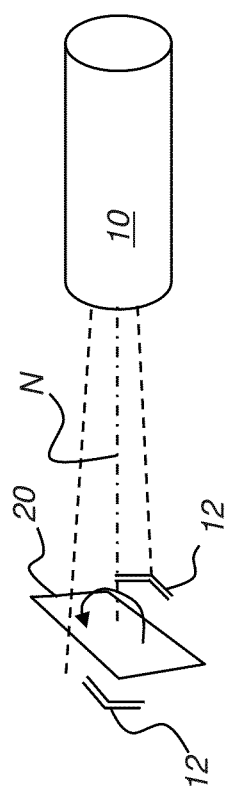

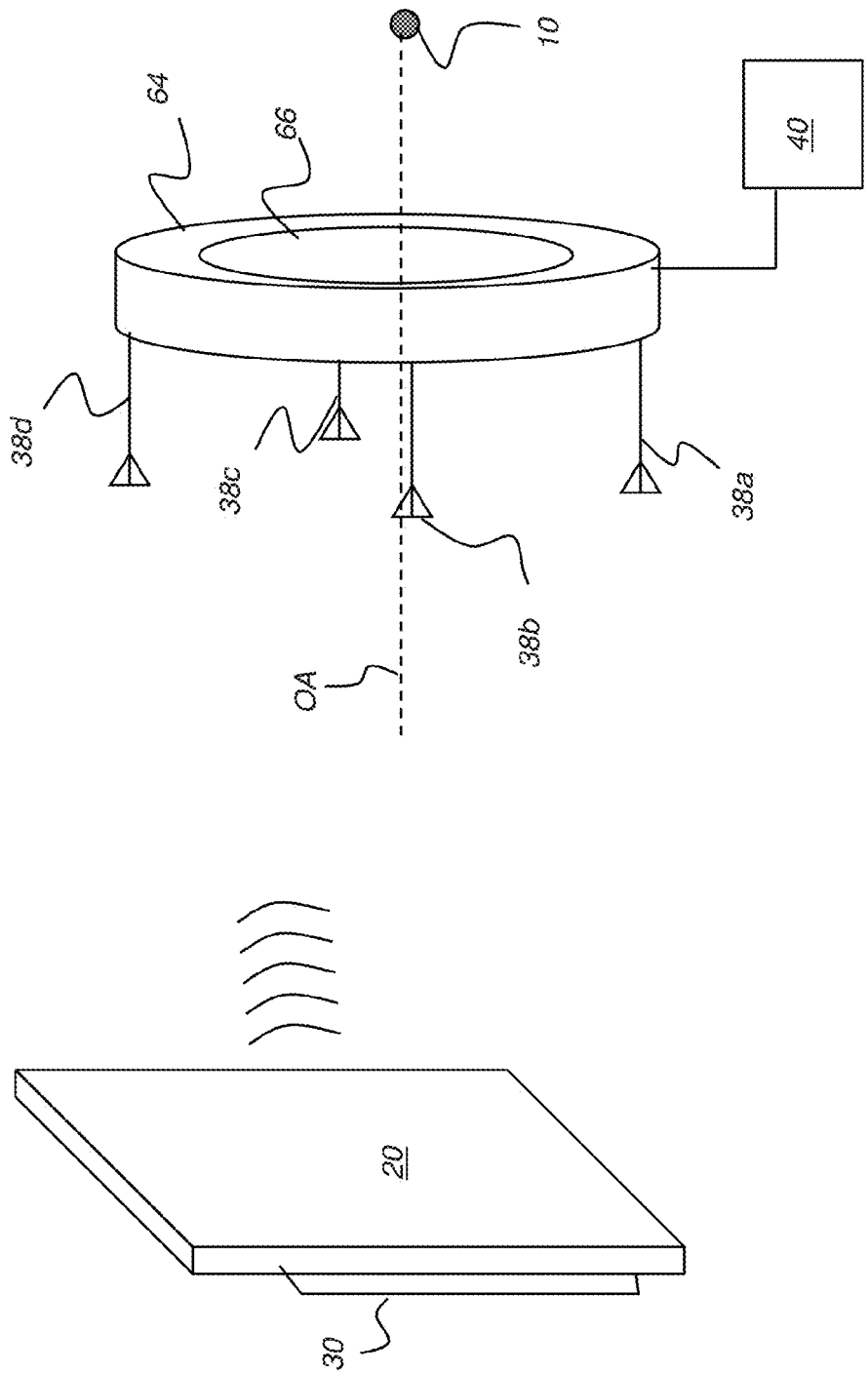

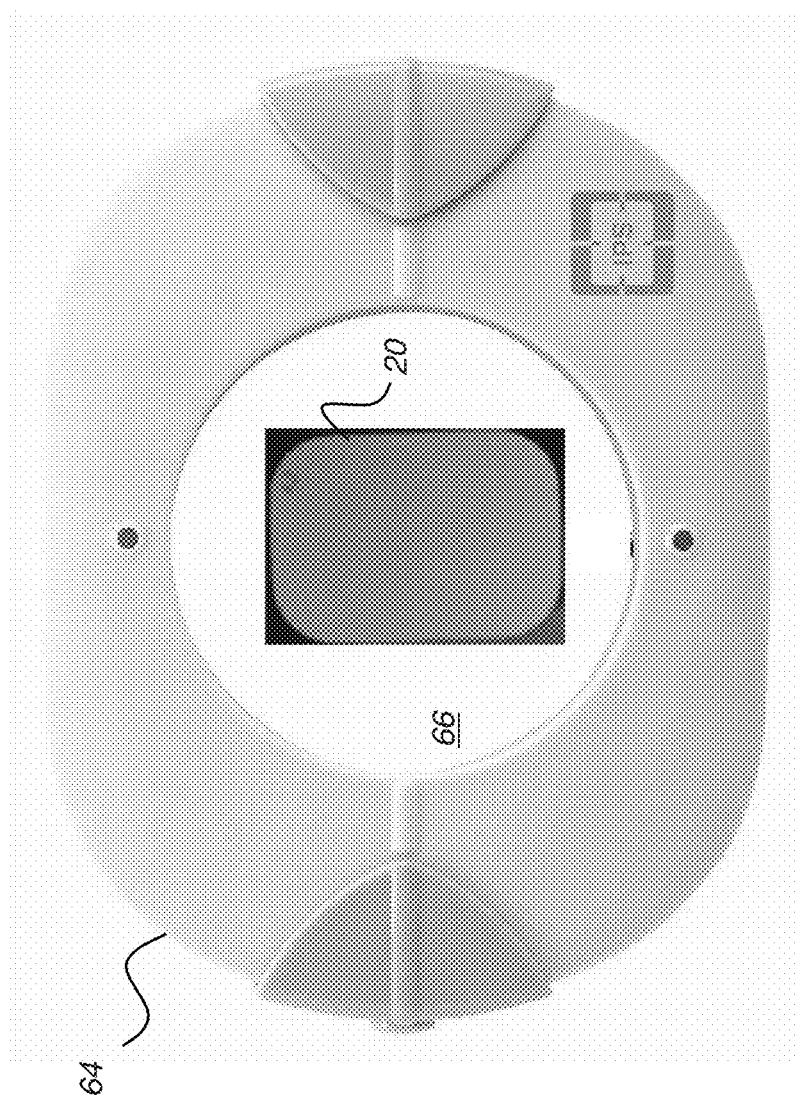

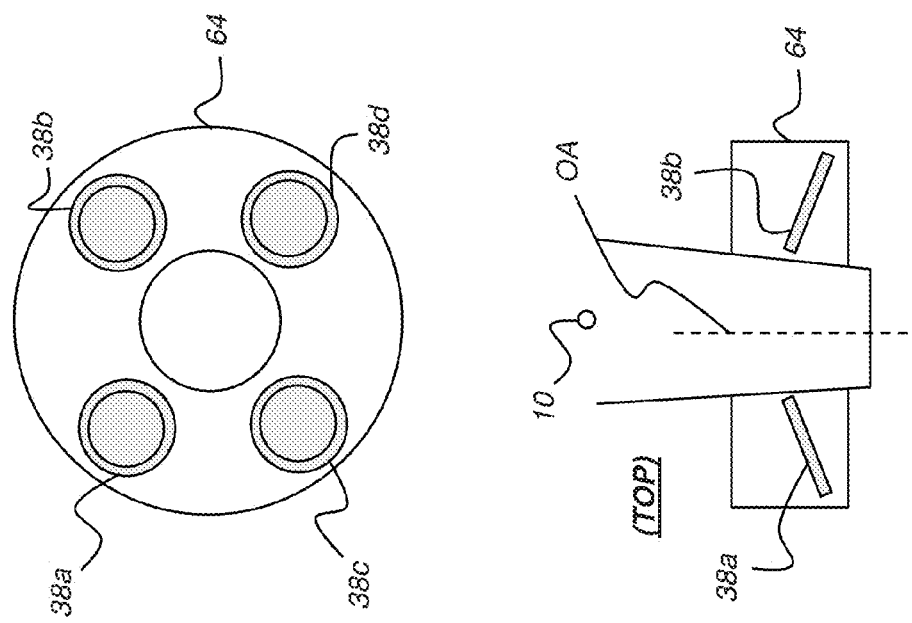

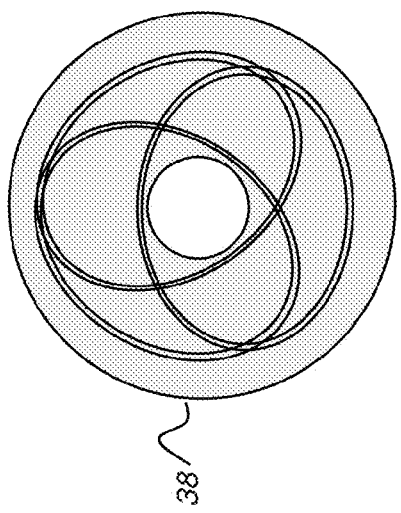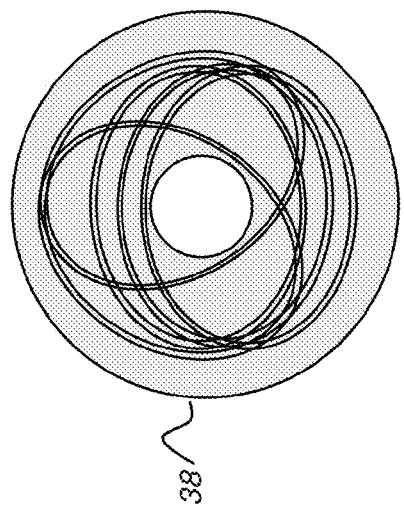
FIG. 8C
FIG. 8D

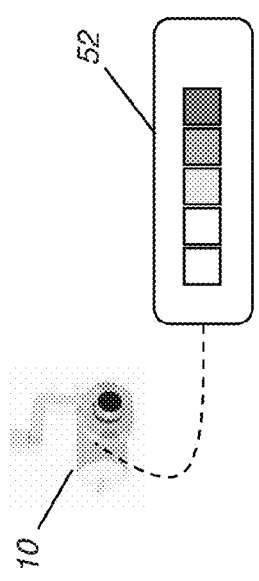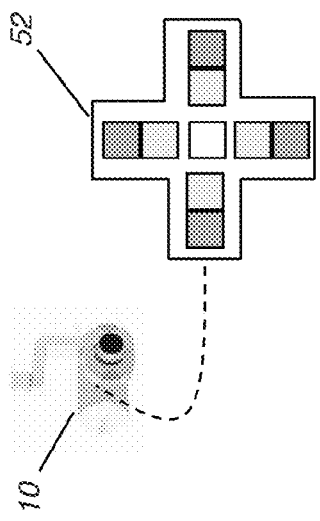
FIG. 10A
FIG. 10B

COMPUTED RADIOGRAPHY POSITIONING METHOD AND SYSTEM

CROSS REFERENCE TO RELATED APPLICATIONS

The present application claims priority to U.S. Provisional Patent Application No. 61/715,862 filed on Oct. 19, 2012 entitled COMPUTED RADIOGRAPHY POSITIONING METHOD AND SYSTEM, to Berger et al., and incorporated herein by reference in its entirety.

FIELD OF THE INVENTION

The present invention relates generally to computed radiography, including medical and dental applications.

BACKGROUND

The use of an information carrier plate (also referred to as a phosphor plate or phosphor storage plate) as a detector for obtaining visually perceptible contrast upon exposure to X-rays is known in the art as computed radiography (CR) and is described for example in U.S. Pat. No. 7,211,785 entitled "SCANNING APPARATUS" to Berger et al., incorporated herein by reference. In Computed Radiography (CR), a phosphor carrier plate is exposed to x-ray or other short-wavelength ionizing radiation and stores a latent image that is read out by a scanning device.

The imaging cycle employing such plates as x-ray detectors comprises juxtaposing the phosphor plate nearby a specific part of the body (e.g., leg, arm, tooth, and the like) and then exposing the plate to X-rays in order to obtain an image from stored radiation energy. Following exposure, the phosphor plate is then removed from the patient and the latent image that is stored thereon is scanned using a stimulating laser beam or other energy source. When it receives the stimulating beam, the illuminated spot on the phosphor plate emits radiation at a second, shorter wavelength, typically in the blue region. The amount of radiation that is emitted upon stimulation is proportional to the amount of energy stored as a result of x-ray exposure. After the plate has been scanned, the obtained image data can be displayed and stored for further examination. The exposed and scanned plate is then erased and can be reused in a subsequent imaging cycle.

Among factors that determine the usefulness and quality of a radiographic image are proper placement of the detector relative to the object that is to be imaged and appropriate positional arrangement of the x-ray source, object, and detector. In conventional radiography, the object is placed between the x-ray radiation source and the detector such as the phosphor plate, and the relative positions of the source and detector are coordinated for proper alignment and angle for obtaining an image. When the object is an arm, leg, or chest of a patient, the x-ray tube, the object to be imaged, and at least portions of the detector are visible to the x-ray technician, so that the task of alignment is straightforward.

Alignment is difficult for dental or intraoral radiography. The detector position is within the patient's mouth and is ordinarily not visible to the technician. The technician typically places the detector into some type of holder, and then inserts the holder into place in the mouth. The holder may have a bite plate or other type of supporting member that helps to position the detector appropriately within the mouth. Holders of this type can be cumbersome and uncomfortable to the patient. Holders and other positioning devices are not error-proof, and positioning errors with these devices can mean that the images obtained are not suitable for use in detecting some types of problems. Poorly aligned detectors can be the cause of problems such as cone cuts, missed apices, and elongation and related angulation or parallax errors, for example. These alignment problems can require re-takes, additional image captures to acquire an acceptable image. Re-takes are undesirable due to the additional x-ray radiation exposure to the patient and because of prolonged patient discomfort with the detector held in the mouth for a longer time period.

Some x-ray sources have included aim indicators that help the technician adjust the position and angle of the x-ray source. Typically, these aim indicators use visible light to trace an outline that helps to center the radiation beam. These work where the radiation detector can be seen, but fall short of what is needed where the detector is not visible, such as with intraoral imaging. The technician must guess or estimate both the position of the intraoral sensor and the angle of incidence of x-rays on the sensor.

The simplified schematics of FIGS. 1A-1E show how misalignment between an x-ray source 10 and a detector 20 can occur. The object being imaged is not shown, since it is removed for improved clarity in describing the alignment problem. For reference in these examples, x-ray source 10 provides visible light aim indices 12 used for aim centering. When correct aim alignment is achieved, shown in FIG. 1A, detector 20 is centered, as shown within aim indices 12. Aim is incorrect at examples shown in FIGS. 1B and 1D.

Proper alignment with respect to angle, or angulation, is desirable. For many types of images, incident radiation from x-ray source 10 is preferably orthogonal to detector 20 as shown in the FIG. 1A example. Line N in FIG. 1A indicates a normal, or orthogonal line, to the surface of detector 20. Examples in FIGS. 1C and 1D show incorrect angular alignment. In example FIG. 1C, aim is correct but angulation is incorrect. In the example of FIG. 1D, both aim and angulation are incorrect. In the example of FIG. 1E, detector 20 is rotated in its own plane.

Note that the schematic examples of FIGS. 1A and 1B assume an orthogonal positioning of x-ray source 10 to detector 20. In some embodiments, an oblique orientation may be preferable. This can complicate the alignment task, since it can be difficult to obtain the desired oblique angle for a detector 20 that is not visible when the patient's mouth is closed.

Positioning a sensor relative to the x-ray source is described in U.S. Pat. No. 7,780,350 entitled "POSITIONING ADJUSTMENT OF A MOBILE RADIOLOGY FACILITY" to Tranchant et al.

At least one drawback of alignment methods relates to lack of guidance for correcting for mis-alignment. The technician needs information in order to correct for mis-alignment and to verify that proper alignment has been obtained. Some methods for reporting the alignment information, such as providing information on an operator console, for example, can be difficult to use when making position adjustments. The technician needs to move back and forth between the operator console and the x-ray tube, checking and correcting each adjustment until proper alignment is achieved.

Thus, there is a need for an apparatus and method for providing improved alignment of the radiation source and image detector in intraoral radiography.

SUMMARY OF THE INVENTION

An object of the present invention is to advance the art of intraoral radiography by providing apparatus and methods that improve the ability to align the radiation source and image detector.

An advantage provided by the present invention is the rapid visualization of adjustment necessary to bring the radiation source and image detector into alignment.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

For one aspect, the present invention provides an apparatus for obtaining an intraoral x-ray image from a patient, the apparatus has an x-ray source and a radio-frequency transceiver coupled to the x-ray source and energizable to transmit an interrogation signal, wherein the transceiver is in signal communication with four or more antennae. An intraoral image detector forms an image upon exposure to radiation received from the x-ray source. A radio-frequency transponder is coupled to the image detector and is configured to respond to the interrogation signal by transmitting a wireless response signal. A control logic processor is in communication with the transceiver and provides an output signal indicative of the spatial position of the image detector according to response signals received from the transponder at the four or more antennae. An indicator responds to the output signal by indicating the relative position of the image detector.

From another aspect, there is provided a method for detecting the relative position of an intraoral imaging detector to an x-ray source for obtaining an intraoral x-ray image from a patient, the method comprising: coupling a radio-frequency transceiver to the x-ray source, wherein the transceiver is energizable to transmit an interrogation signal; coupling four or more antennae to the radio frequency transceiver, wherein the four or more antennae are spaced at equal intervals about an optical axis of the x-ray source; coupling a radio-frequency transponder to the imaging detector, wherein the transponder is configured to respond to the interrogation signal by transmitting a wireless response signal; providing an output signal indicative of the spatial position of the image detector according to the response signals received from the transponder at the four or more antennae; and responding to the output signal by displaying an indicator indicating the relative position of the image detector.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 1A, 1B, 1C, 1D, and 1E are simplified schematic block diagrams that show different aspects of the source-to-detector alignment problem.

FIG. 5A is a perspective diagram that shows some of the spatial relationships of positioning system components.

FIG. 5B is a plan view that shows a ring and a centered detector according to an embodiment of the present invention.

FIG. 7A shows top and plan views of antenna apparatus according to embodiments of the present invention.

FIGS. 8A-8D are plan views showing different antenna arrangements.

FIG. 10A is a plan view that shows an indicator used on the x-ray source for reporting needed alignment adjustment.

FIG. 10B is a plan view that shows an alternate embodiment of an indicator used on the x-ray source for reporting needed alignment adjustment.

DETAILED DESCRIPTION OF THE INVENTION

Figure 2:
FIG. 2 shows a typical dental treatment room.

The following is a detailed description of the preferred embodiments of the invention, reference being made to the drawings in which the same reference numerals identify the same elements of structure in each of the several figures.

Figures shown and described herein are provided in order to illustrate key principles of operation according to the present invention. Some exaggeration of relative dimensions and scale may be necessary in order to emphasize basic positional and structural relationships or principles of operation.

Where they are used, the terms "first", "second", and so on, do not necessarily denote any ordinal or priority relation, but may be used for more clearly distinguishing one element or time interval from another. In the context of the present disclosure, the terms "operator", "technician", "user", and "practitioner" are considered to be equivalent.

In the context of the present disclosure, the equivalent terms "image detector", "imaging detector" or simply "detector" refer to the element that is placed in the patient's mouth, that receives radiation, and that provides the image content. Such a detector may be a photosensitive film element having a piece of film enclosed in a sleeve or film holder, wherein the film is separately developed to provide the x-ray image. The detector can be a phosphor storage element that is separately scanned to provide x-ray image data, or a digital detector that provides the x-ray image data directly to an imaging system.

In the context of the present disclosure, the equivalent terms "flexible information carrier plate", "flexible plate", "CR plate", "image plate", "imaging plate" "carrier plate", "storage phosphor plate", "phosphor plate" or simply "plate" refer to photo-stimulable phosphor plates (PSP plates) that are used for image storage in the computed radiography (CR) arts, deployed in a manner analogous to the photographic plates that they have replaced in many applications. The information carrier plate is considered flexible when it has at least some degree of conformance to curvatures useful for intraoral imaging.

In the context of the present disclosure, the term "scanner" or "scanning device" refers to a device or apparatus that is capable of obtaining stored image data from the flexible information carrier plate following exposure of the plate. The scanner typically stimulates the phosphor storage media using a laser beam. As the beam energy passes over the plate surface, it frees electrons "trapped" in "color centers" in the crystal lattice of the X-rayed phosphor plate. The light emitted during laser stimulation can be collected and the resulting signal converted into a digital image by a computer or other dedicated logic processor. The location at which the scanner is deployed is referred to herein as a scanning station.

As the simplified schematic of FIGS. 1A through 1E illustrates, lateral (side-to-side) position of detector 20 and angulation of the detector 20 inside the patient's mouth are among factors that are relevant in achieving alignment. Rotation of the detector within its plane (that is, rotation about orthogonal axis N) as shown in FIG. 1E is typically of less significance, but can be a consideration for maintaining the desired alignment. For the mis-alignment conditions shown in FIGS. 1A-1E, it can be difficult for the technician to determine in which direction to adjust the detector position or the x-ray source and how much readjustment is needed.

Referring now to FIG. 2, there is shown a typical dental treatment room 100 of a practitioner. The treatment room, inter alia, comprises a treatment chair 102 having a console with various instruments as required for dental treatment, e.g. intra-oral treatment.

The treatment room is equipped with a suitable interface terminal that serves as a processing and acquisition station for input, output, and management of data and possibly including a keyboard with mouse. It is not shown specifically but should be appreciated that the interface communicates over a network, for example, via a local Ethernet network, with a suitable server providing access to a database and a software application enabling management of medical and personal data related to a medical case. The application allows acquisition, viewing, and processing of images obtained after scanning, archiving the images and related data, and other functions. In an alternate embodiment, such as in a small clinic, the interface may communicate with a local computer workstation or personal computer (PC), instead of with a networked server.

The treatment room is suitable for computed intra-oral dental radiography and is equipped with a monitor 106, e.g., an LCD (Liquid Crystal Display) for displaying images acquired after X-ray exposure and scanning. It is not shown in FIG. 2 but should be appreciated that a plurality of flexible information carrier plates are available, typically stored in the vicinity of the treatment chair.

It is appreciated that the treatment room can comprise an X-ray generator, which may be situated either in the treatment room itself or adjacent thereto. In a small treatment room, a scanner can also be provided for obtaining the stored image data obtained after exposing the information carrier plates to X-rays. However location within the treatment room is not compulsory, since the practitioner can alternately use a scanner that is situated apart from the treatment room.

In the present disclosure, the treatment room is alternately referred to as a working station. If the working station is equipped with a scanner dedicated solely to this station, then the possibility for mismatch of the plates is less likely. This possibility, however, still exists and therefore it would be desirable to render the plates identifiable in some way even for such a basic system.

As noted previously in the background material, proper positioning and alignment of the phosphor carrier plate relative to the x-ray source/tube is relevant to the acquisition of the x-ray image. However, when the phosphor plate is positioned within the mouth of a patient, it is difficult to determine whether the phosphor plate is appropriately aligned with the x-ray source/tube. Embodiments of the present invention use information from signals emitted from the carrier plate in order to determine relative position of the x-ray source and detector and provide instructive information for adjustments to correct mis-alignment.

Radio Frequency Identification Devices (RFID devices) are known for identification, tracking, and monitoring in various applications. RFID tracking is used for local identification of various items, like consumer goods, reusable and disposable items, as well as for identifying and tracking people, animals, and the like. This identification technology has been implemented in medical and dental apparatus and for various other types of technical and non-technical equipment and processes.

An RFID system comprises two main components: (i) a transponder associated with an item to be identified, and (ii) an interrogator, separated from the transponder by a short distance. The RFID interrogator comprises an antenna, a transceiver and a processing device. The interrogator component sends RF energy and an interrogating signal (if necessary) to the transponder and then receives an RF response signal from the transponder. The received signal is transferred to the processing device and is read.

As generally used, the RFID transponder, or so-called RFID tag, is affixed by a suitable method to the item to be identified and comprises an integrated circuit containing RF circuitry. This circuitry provides a memory for storing information to be transmitted as a signal to the processing device in the interrogator. The RFID tag also comprises an antenna for transmitting this signal. Reading the signal that has been sent by the transponder allows the item bearing the tag to be identified and monitored.

In the context of the present disclosure, the term "RFID system", or "RFID device" refers to a device having two main components: (i) a RFID transponder associated with an item to be identified, and (ii) an RFID interrogator, separated from the transponder by a short distance. The interrogator comprises a transceiver with its corresponding antenna and a processing device or interface that executes commands to communicate with the RFID transponder. The interrogator component sends one or more RF signals to the transponder and then receives corresponding RF response signals from the transponder. A received signal is transferred to the processing device and is interpreted.

In the context of the present disclosure, the term "RFID tag", or "RFID transponder" refers to a transponder that is affixed to, encased within, or otherwise coupled by a suitable method to x-ray detector 20 and comprises RF circuitry for signal reception and transmission, typically also including an integrated circuit. The RFID tag also comprises an antenna for transmitting this signal.

According to an embodiment of the present invention, information may be stored in the RFID tag and transmitted upon interrogation by the RFID transponder. However, of particular interest for positioning and alignment, using the method of embodiments of the present invention, is the signal strength from the RFID transmission, rather than this information content. The positioning system of embodiments of the present invention adapts a technology known as RSSI (received signal strength indicator) for the particular purpose of indicating detector 20 position and orientation. In telecommunications, RSSI is a technology for assessing the power that is present in a received radio signal. RSSI is a generic radio receiver technology metric, which is typically invisible to a user of the device containing the receiver, but is known to users of wireless networking, for example, as used in the IEEE 802.11 protocol. Results of assessments made using RSSI are expressed in arbitrary units, rather than using standard values, based on comparing two or more signals in a given case.

RSSI can be accomplished in an intermediate frequency (IF) stage before the IF amplifier. In zero-IF systems, RSSI measurement is typically accomplished in the baseband signal chain, before the baseband amplifier. RSSI output is often a DC analog level that is representative of comparative signal strength. The RSSI output signal can be sampled by an internal analog-to-digital converter (ADC) and the resulting codes made available directly or by means of a peripheral or internal processor bus.

The end-user (for example, the dental technician) may observe an RSSI value when measuring the signal strength of a wireless network using a wireless network monitoring tool like Wireshark network protocol analyzer, Kismet device or in SSIDer scanner (from MetaGeek, Boise, Id.). Results are reported over an arbitrary range of values. As an example, Cisco Systems cards have an RSSI_Max value of 100 and thus report 101 different power levels, where the RSSI value is 0 to 100. Another popular Wi-Fi chipset is made by Atheros (Qualcomm Atheros Inc., San Jose, Calif.). An Atheros based card returns an RSSI value of 0 to 127 (0x7f) with 128 (0x80) indicating an invalid value. There is no standardized relationship of any particular physical parameter to a corresponding RSSI reading. The IEEE 802.11 wireless networking standard does not define any relationship between RSSI value and power level in mW or dBm. Vendors provide their own accuracy, granularity, and range for the actual power (measured as mW or dBm) and their range of RSSI values (from 0 to RSSI_Max). The subtlety of 802.11 RSSI comes from how it is sampled; RSSI is acquired during the preamble stage of receiving an 802.11 frame.

In order to better understand the parts and operation of the apparatus of the present invention and how the use of signal strength is advantaged, it is helpful to show how proper alignment can be detected by an imaging system using conventional triangulation methods. Referring to the block diagram of FIG. 3, there is shown an intraoral imaging apparatus 22 that detects alignment of imaging detector 20 with x-ray source 10. In the FIG. 3 arrangement, detector 20 is placed adjacent to a tooth 14, behind a cheek 18 of the patient, shown in cross-section. Incorporated as part of detector 20 are a number of RF transponders 30, such as RFID tags. RF transponders 30 are typically spaced apart from each other in order to provide triangulation information. A sensor 24, itself aligned and positionally coupled with x-ray source 10, senses the presence of RF transponders 30 by sensing emitted RF signals. Methods for energizing and sensing RF transponders, such as the tiny emitters used in RFID tags, for example, are well known to those skilled in the signal detection arts. A control logic processor 26, in signal communication with one or more sensors 24, employs conventional trigonometric calculations based on the received signals from, or other detectable features of, transponders 30 and the known position of sensor 24 with relation to x-ray source 10. This is performed in order to determine the corresponding positional and angular alignment of detector 20 in the patient's mouth relative to x-ray source 10. An operator console display 28 then indicates alignment information for the operator and may recommend the needed adjustment settings. Sensors 24 are energizable to receive electromagnetic signals of one or more predetermined frequencies.

Figure 3:
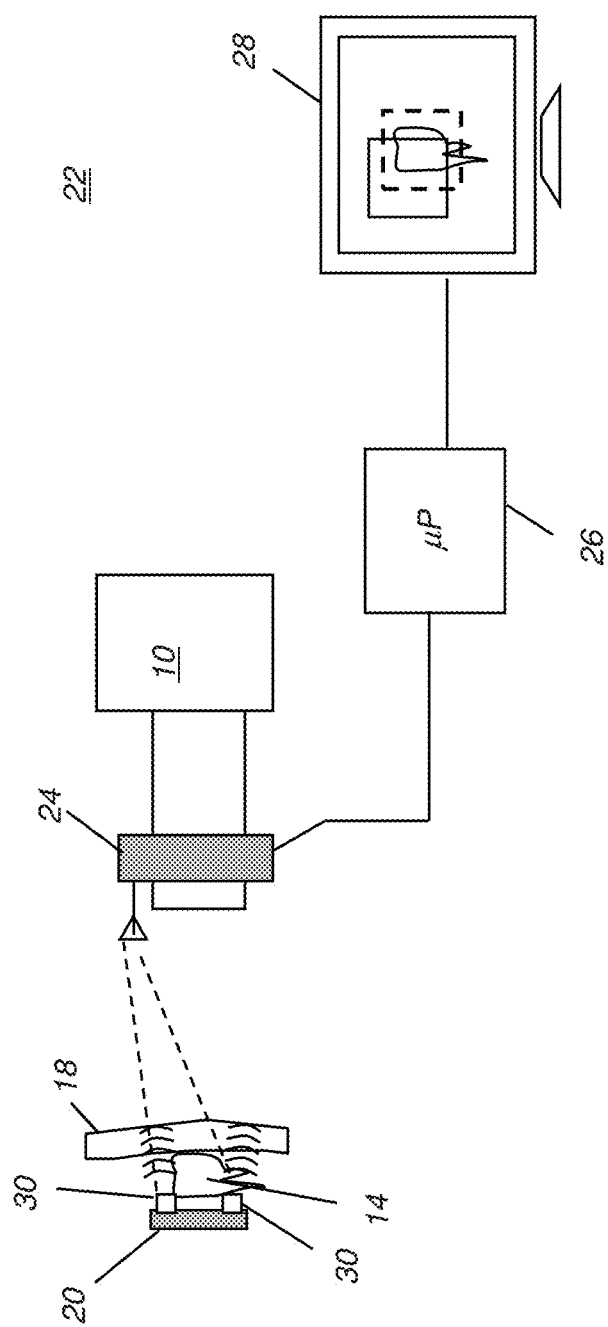
FIG. 3 is a schematic block diagram for an intraoral imaging apparatus using multiple emitters on a detector.

The conventional triangulation methods used in the FIG. 3 embodiment are workable, but require multiple RF transponders 30 operating in a coordinated manner in order to provide the needed triangulation data. Moreover, the RF transponders must be well-matched or precisely calibrated with each other in order to obtain meaningful angular and relative distance information.

Embodiments of the present invention improve upon the basic system of FIG. 3 using only a single RFID transponder that is mechanically coupled to x-ray detector 20 that is placed within the mouth of the patient. The transceiver that communicates with the RFID transponder is coupled to x-ray source 10 according to an embodiment of the present invention. The transceiver circuitry uses multiple antennas for sensing, at different positions relative to the x-ray source, the relative signal strength from the signal that is emitted from the RFID transponder. Analysis of detected signal strength levels then enables control logic to calculate and display any needed positional adjustments. Characteristics of the signal emitted by a single RFID transponder are thus used to obtain enough information to determine position, angular orientation, and centering of the detector relative to the x-ray source 10. As a result, the technician can direct more attention to detector 20 placement in a suitable position within the patient's mouth and adapt to the detector position by moving the x-ray source 10 appropriately.

According to an alternate embodiment of the present invention, the transceiver and positioning system are not mechanically coupled to x-ray source 10, but are mechanically coupled to some other reference point. For such an embodiment, a computer or other type of control logic processor tracks the positions of both x-ray source 10 and detector 20 and provides signals that help the operator to adjust source and detector positioning appropriately.

Triangulation calculation is considerably more complex if such an arrangement is used. Additional transponders (not shown) or alternate positioning sensors would be required for x-ray source 10 in such an embodiment.

Figure 4A:
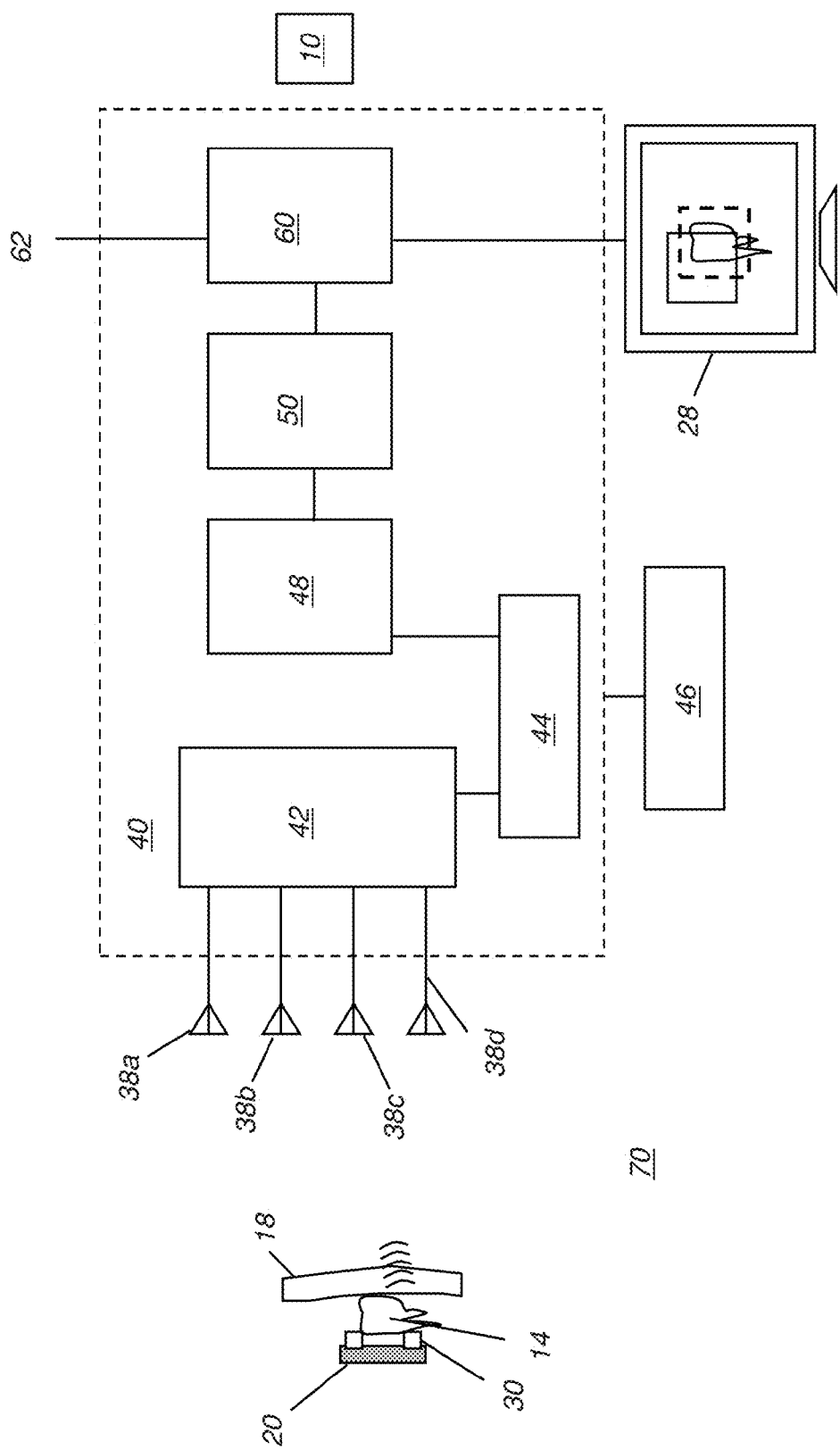
FIG. 4A is a schematic block diagram showing a positioning system for an intraoral imaging apparatus according to an embodiment of the present invention.

The schematic block diagram of FIG. 4A shows components of a positioning system 40 for adjusting the position of x-ray source 10 in an intraoral imaging apparatus 70 according to an embodiment of the present invention. Antennae 38a, 38b, 38c, and 38d are provided and are distributed to direct the transceiver signal to a single RF transponder 30 and to obtain signals from the single RF transponder 30 that is coupled to detector 20. A multiplexer 42, working in conjunction with an impedance matching circuit 44, provides transponder signal output to RF transceiver circuit 48 from each of the antennae 38a, 38b, 38c and 38d, in sequence. An RFID reader 50 reads the obtained RF signals received by transceiver circuit 48 and works with a control logic processor 60 to determine relative position according to RF signal strength at the different antennae. An optional input 62 for external program data or signal is also provided. Input 62 can be used, for example, to provide auxiliary signals or data that are useful for the positioning logic. According to an embodiment of the present invention, input 62 provides control logic processor 60 with coordinate information related to the position of x-ray source 10. This data can be obtained from sensors (not shown) coupled to source 10 or to its support structure. Input 62 can also provide addressing information specific to RF transponder 30, such as a unique identifier or other code, for example. According to an alternate embodiment of the present invention, input 62 provides alternate or updated instructions for control logic processor 60.

Figure 4B:
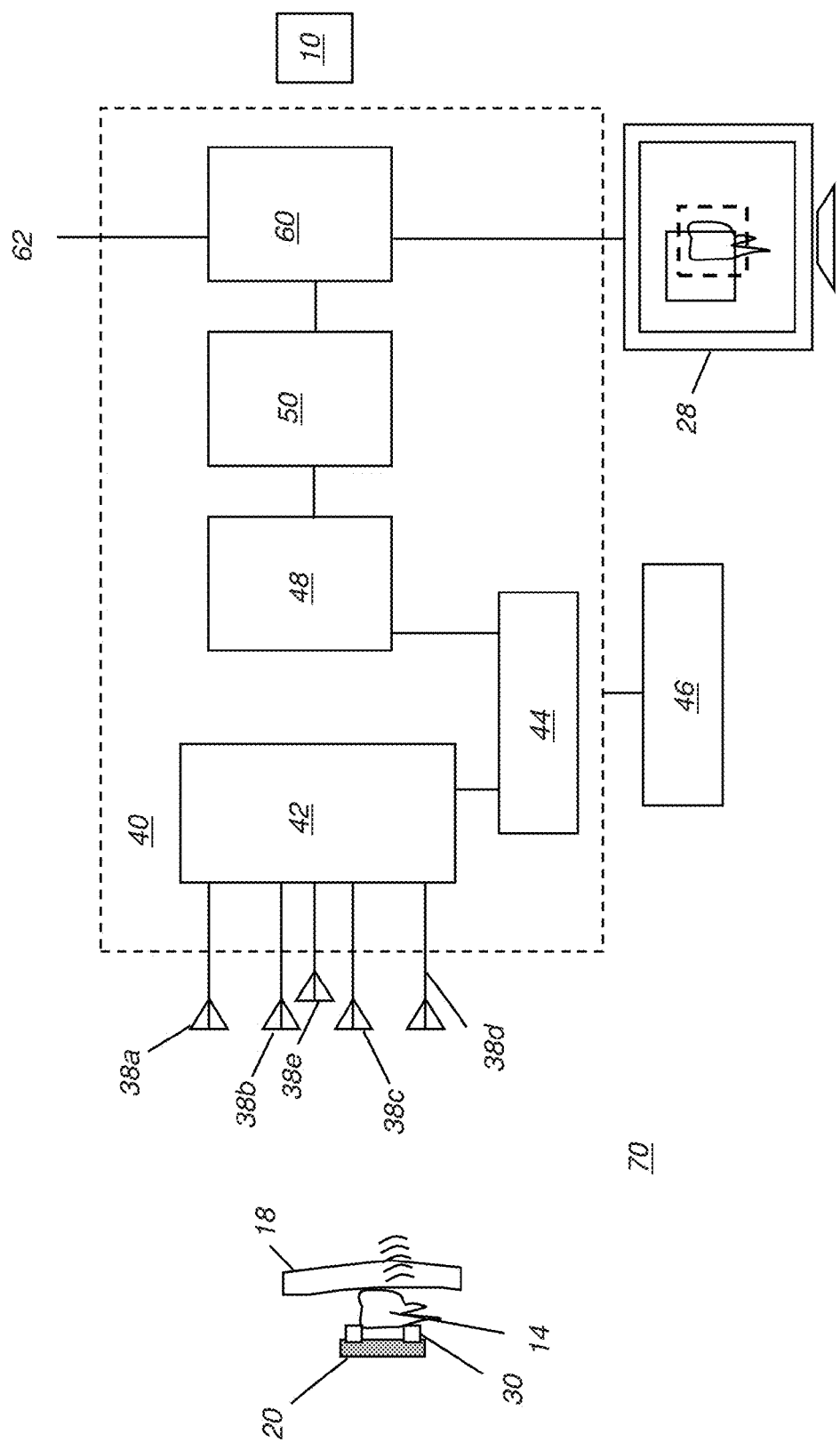
FIG. 4B is a schematic block diagram showing a positioning system for an intraoral imaging apparatus that reads the transponder signal in parallel, according to an alternate embodiment of the present invention.

The schematic diagram of FIG. 4B shows an alternate embodiment in which a separate antenna 38e is used to transmit the transceiver signal to RF transponder 30. The other antennae 38a-38d are then used to sense the response signals from transponder 30 in parallel, rather than sequentially, as described with reference to the FIG. 4A arrangement. This enables the signal sensing to be executed more rapidly.

Display 28 is provided and is in signal communication with control logic processor 60 to provide any needed adjustment information, as described in more detail subsequently. A power supply 46 provides power to positioning system 40.

The schematic block diagram of FIG. 5A and plan view of FIG. 5B show some of the spatial relationships of positioning system 40 components. Antennae 38a, 38b, 38c, and 38d are distributed about a ring 64 to obtain the RF transponder 30 signal. Ring 64 is formed about an aperture 66. RSSI technology is used to determine the relative position of detector 20 according to the received signal strength. FIG. 5B shows ring 64 and a centered detector 20 according to an embodiment of the present invention. Detector 20 is seen through the aperture 66. Antennae are not seen since they are integrated within ring 64 in the embodiment shown.

With reference to FIGS. 4A, 4B, and 5A, embodiments of the present invention sense the relative signal strength from transponder 30 at four or more antennae 38a, 38b, 38c, and 38d and use this information to determine the position of detector 20 relative to positioning system 40. Upon receipt of an initiating RF signal from transceiver circuit 48, transponder 30 emits an RF signal. Each of antennae 38a, 38b, 38c, and 38d obtain this emitted signal and provide the signal to positioning system 40 components. In the FIG. 4A embodiment, each signal is sampled separately, as controlled by a multiplexer 42. Alternately, using the FIG. 4B embodiment, signals can be sampled in parallel. Control logic processor 60 analyzes the relative signal strength from each antenna in order to derive positional data. RSSI signal analysis techniques use relative signal strength for obtaining spatial coordinate data. Signal strength is related to relative position, since signal strength has an inverse square relationship to the distance between the emitter and receiver. By considering the relative signals between pairs of respective antennae, triangulation is used to obtain positional coordinates. The use of more than four antennae provides additional triangulation data that allows an even higher degree of positioning accuracy. The relative size of ring 64 can be a factor in determining the available accuracy; generally, the inner aperture diameter of ring 62 should be larger than the size of detector 20, with sufficient spacing between antenna locations to allow for some tolerance in error measurement; if antennae are spaced too closely together, it can be difficult to accurately sense signals that have slightly different signal strength. Even spacing of four antennae about aperture 66, with one antenna at each 90 degree position about the aperture, and with the aperture centered along optical axis OA of source 10, provides a suitable arrangement for triangulation.

Triangulation techniques for and the use of relative signal strength for determining the distance, spatial position, and orientation of an emitter are well known to those skilled in the position-sensing arts. A system using four omnidirectional antennae can determine both a transmitter's power level and the Cartesian coordinates (x,y,z) of the transmitter when the RSSI information is obtained. Some amount of initial calibration can be performed in order to compensate for differences in antenna sensitivity and signal handling for each antenna.

It should be noted that fewer than four antennae could be used for triangulation where relative movement of the x-ray source is restricted to the plane of the detector. In such a case, three antennae could be used, spaced at 120 degree increments in the plane. However, this type of arrangement can be impractical and constraining for general-purpose dental imaging.

For high-accuracy positioning, it is useful to know the relative position of RF transponder 30 with respect to detector 20 with which it is coupled. According to an embodiment of the present invention, RF transponder 30 is positioned at or near the center of detector 20. This centered arrangement is particularly suitable where detector 20 is deployed on a flexible substrate. Transponder 30 can alternately have some other position, such as near a corner of detector 20. Control logic processor 60 then calculates the appropriate offset adjustment for this transponder 30 position. However, it should be noted that some slight bending of a flexible detector 20 along its edges can cause positioning error if transponder 30 is not centered on the detector.

Figure 6A:
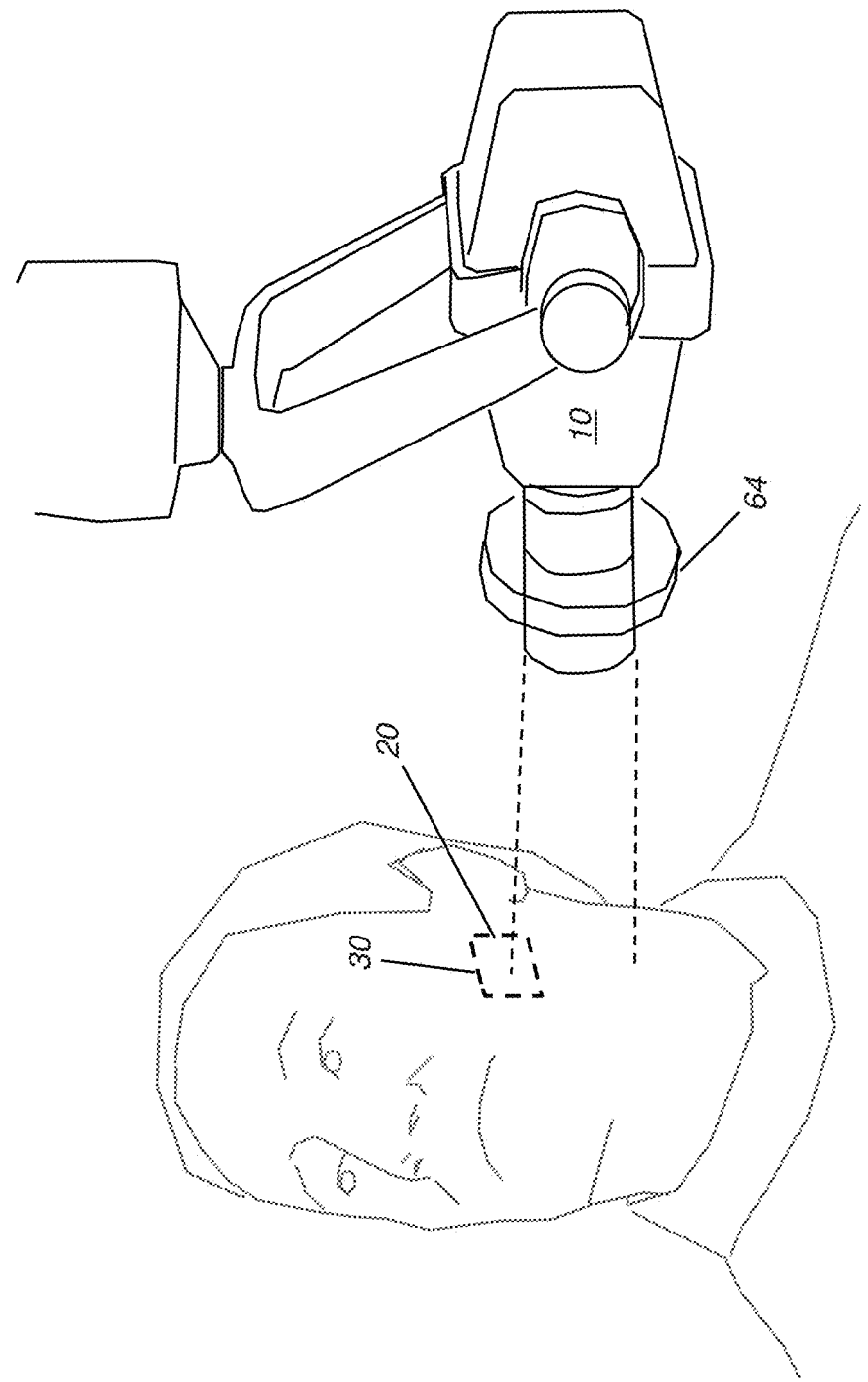
FIG. 6A is a perspective view that shows the relative positions of an intraoral detector and a mis-aligned x-ray source.
Figure 6B:
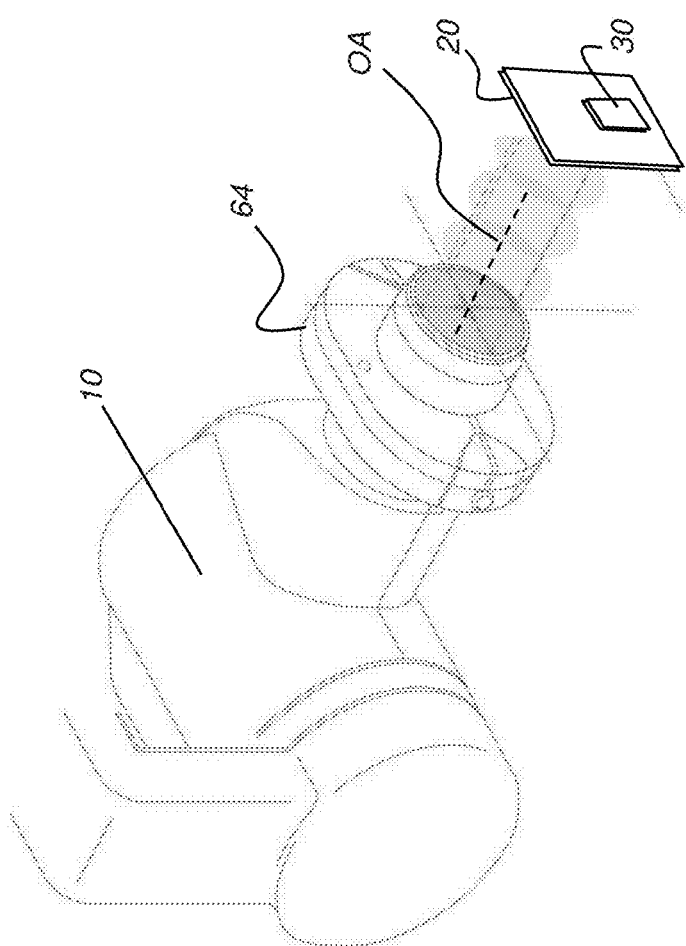
FIG. 6B is a perspective view that shows components of the positioning system for the x-ray source.

FIG. 6A is a perspective view that shows the relative positions of intraoral detector 20 and a mis-aligned x-ray source 10. It can be appreciated that it is difficult for the technician or other operator to determine whether or not alignment is correct and, if in error, how much adjustment to provide. FIG. 6B is a perspective view from an alternate angle that shows components of the positioning system that are correctly aligned for imaging at detector 20 using x-ray source 10. The optical axis OA is shown at the cross hairs in FIG. 6B. The x-ray beam is generally centered about optical axis OA.

Figure 7B:
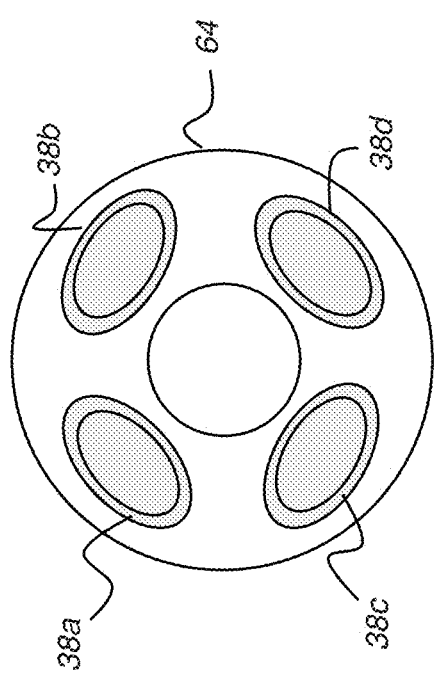
FIG. 7B shows a plan view of antenna apparatus according to an alternate embodiment of the present invention.
Figure 8A:
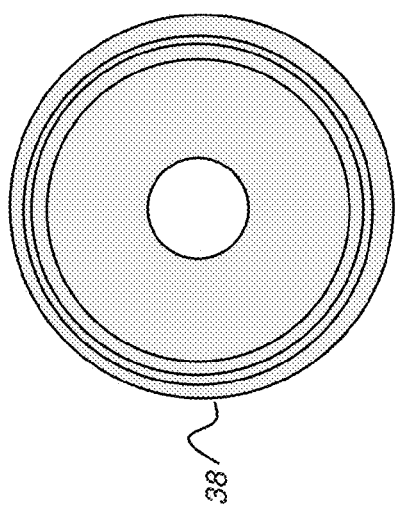
Figure 8B:
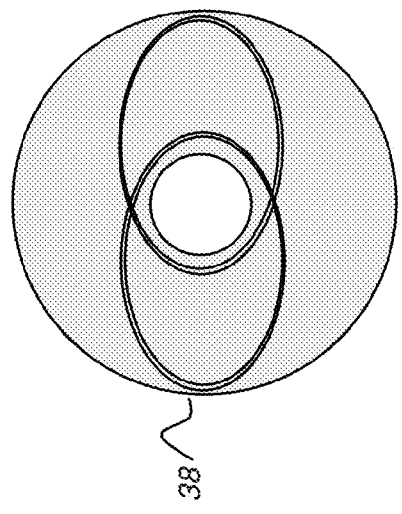

A number of different antenna arrangements are available. FIG. 7A shows top and plan views of antenna apparatus according to an embodiment of the present invention. Antennae 38a and 38b can be planar, situated on ring 64 such that they are lying in planes slanted at an oblique angle relative to optical axis OA or relative to the equipment that directs radiation from x-ray source 10. An oblique angle is an angle that is at least 2 degrees or more from normal. FIG. 7B shows an alternative arrangement of four antennae 38a, 38b, 38c, and 38d. Ring 64 can have any of the alternate antennae arrangements shown, or may have some other arrangement of antennae 38a-38d. In addition, more than four antennas can be provided for transmitting RF signals used for position detection.

FIGS. 8A, 8B, 8C, and 8D are plan views showing different antenna 38 arrangements. The use of wire coils allows more compact and efficient antennae to be designed. This can be advantageous, for example, where it is desired to have a more streamlined design or for system ergonomics.

Figure 9A:
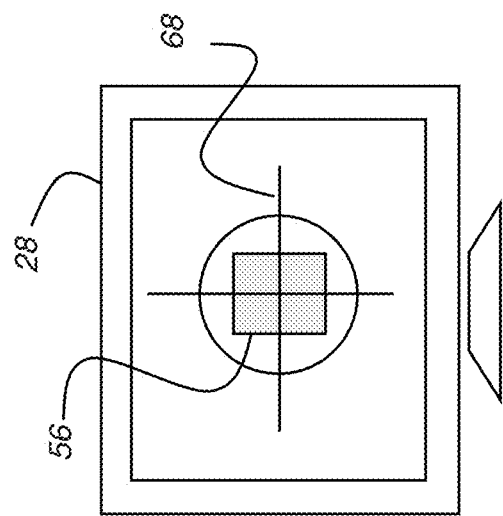
FIG. 9A is a plan view of a display that shows poor alignment for the intraoral detector using the positioning system of the present invention.
Figure 9B:
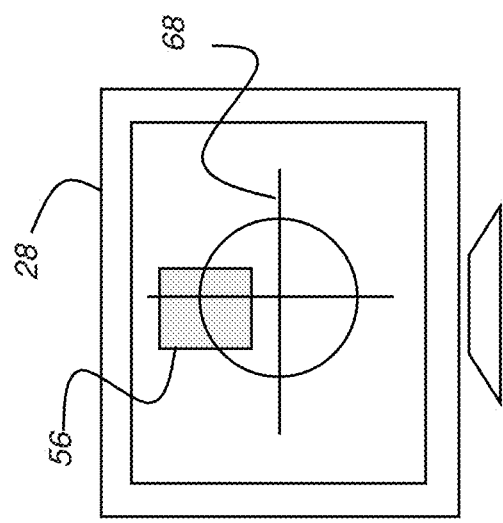
FIG. 9B is a plan view of a display that shows good alignment for the intraoral detector using the positioning system of the present invention.

Once the relative position of detector 20 is determined, positioning system 40 of the present invention provides the operator with information on suggested adjustments to improve alignment. As shown in FIG. 9A, display 28 acts as an indicator that shows poor alignment for the intraoral detector using the positioning system of the present invention. Cross hairs 68 indicate the optical axis of the x-ray beam. An icon 56 on the display indicates a misalignment condition. FIG. 9B is a plan view of a display that shows good alignment for the intraoral detector using the positioning system of the present invention, with detector icon 56 centered with respect to cross hairs 68.

The positioning system 40 of the present invention alerts the operator to an alignment problem and provides indicators that show the adjustment direction and, optionally, relative amount of adjustment needed. Display 28, for example, has a blinking or otherwise highlighted icon 56 or other cursor that acts as an indicator and provides adjustment instructions. Referring to the plan view of FIG. 10A, an indicator or guide 52 associated with the x-ray source 10 is used for reporting needed alignment adjustment. The operator can adjust the positioning of the head of x-ray source 10 according to the appearance of guide 52. FIG. 10B is a plan view that shows an alternate embodiment of guide 52 associated with the x-ray source for reporting needed alignment adjustment. Blinking or highlight color within guide 52 assist the operator in determining the needed movement direction for improving the centering of x-ray source 10.

Figure 11:
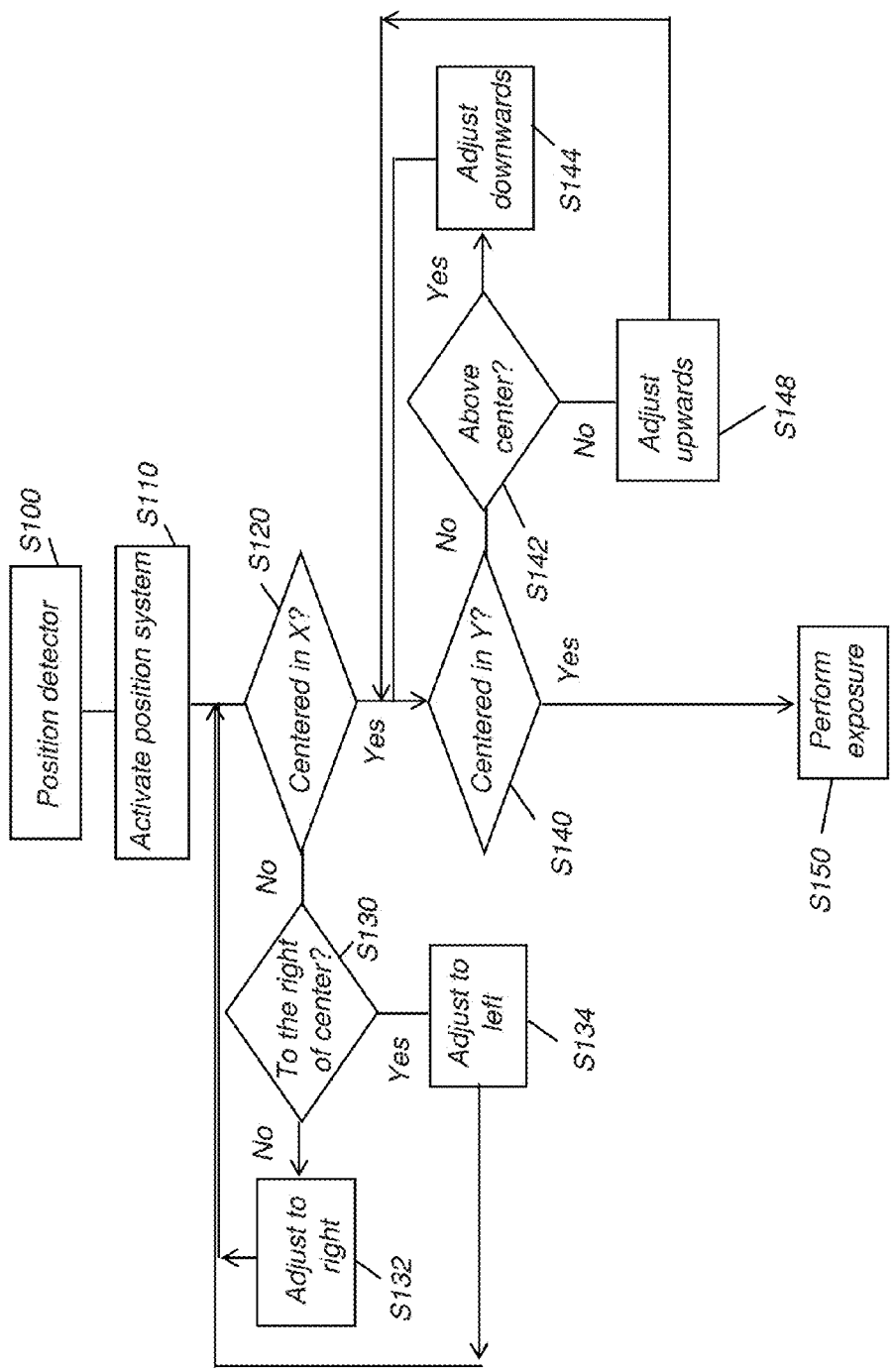
FIG. 11 is a logic flow diagram that shows the sequence for alignment of the x-ray source prior to exposure according to an embodiment of the present invention.

FIG. 11 is a logic flow diagram that shows the sequence of steps required for alignment of the x-ray source prior to exposure. In a detection step S100, the technician places the intraoral detector into the patient's mouth at the proper orientation. An activation step S110 then activates the positioning system 40 for determining and reporting the amount of misalignment. A decision step S120 determines whether or not the detector 20 is centered relative to the x-axis in the plane orthogonal to the path of the x-ray radiation. If centering is incorrect, a decision step S130 checks to determine whether or not the detector 20 is relatively to the right of center for the x-ray head. The operator/technician makes the needed adjustments, if any, in an adjustment step S132 or S134, as appropriate. Another decision step S140 checks for y-axis centering and calls a decision step S142 to determine which of subsequent adjustment steps S144, S148 are needed. An exposure step S150 can then be executed when the x-ray source is properly centered on the detector.

In general, because of the nature of the dental imaging environment, manual adjustment of the position of x-ray source 10 is used. For this reason, guidance provided by system control logic is particularly useful, allowing the operator to make slight adjustments and recheck system indicators, such as those shown in FIGS. 9A and 9B or those provided on the system itself, such as those shown in FIGS. 10A and 10B. In addition, slight readjustment of patient position can also be performed by the technician. In an alternate embodiment, some automation of the adjustment may also be provided, such as using optional stepper motors coupled to the positioning mechanism for x-ray source 10 (not shown).

Software executing on control logic processor 60 (FIGS. 4A, 4B) or on an external computer device controls a number of the functions shown in the logic flow diagram of FIG. 11. This includes position system activation in activation step S110 and calculations in x-axis decision step S120, along with generating signals in step S130 that are used to indicate any needed adjustment for the operator. Similarly, software provides the functions of decision step S140 for y-axis centering and adjustment in step S142. Software can also control whether or not exposure step S150 executes, based on centering information.

Once exposure takes place, the intraoral detector 20 can be removed from the patient's mouth and the image obtained.

Color can be used to help indicate the relative amount of alignment offset in various ways. For example, even with the outline of detector 20 displayed on the display 28 monitor, it can be difficult for the technician to know how to adjust for angular alignment. Display of instructions in different colors can help to guide the technician in adjusting the angle of the x-ray tube until the desired adjustment is obtained.

For example, one could contemplate employing the present invention not merely in dental radiography but also in other computer radiography applications, where RFID devices are available. Such applications may include for example, but are not limited to, orthopedic radiography, chest radiography, skull radiography, spine radiography, and the like.

An apparatus for obtaining an intraoral x-ray image from a patient comprises an x-ray source; a radio-frequency transceiver coupled to the x-ray source and energizable to transmit an interrogation signal, wherein the transceiver is in signal communication with four or more antennae; an intraoral image detector that forms an image upon exposure to radiation received from the x-ray source; a radio-frequency transponder that is coupled to the image detector and is configured to respond to the interrogation signal by transmitting a wireless response signal; a control logic processor that is in communication with the transceiver and that provides an output signal indicative of the spatial position of the image detector according to response signals received from the transponder at the four or more antennae; and a display that responds to the output signal by indicating the relative position of the image detector. The intraoral image detector can be a photosensitive film imaging device, a storage phosphor imaging device, and a digital detector device. The display can further indicate a recommended adjustment of the relative position of the image detector. The four or more antennas can be encased.

Consistent with an embodiment of the present invention, a computer program utilizes stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation or can be executed by a microprocessor operating as control logic processor 60 (FIG. 4A, 4B). However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various control algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the positioning systems art.

The invention has been described in detail with particular reference to certain preferred embodiments thereof, but it will be understood that variations and modifications can be effected within the scope of the invention.

The invention claimed is:

1. An apparatus for obtaining an intraoral x-ray image from a patient, the apparatus comprising:
   an x-ray source;
   a radio-frequency transceiver coupled to the x-ray source and energizable to transmit an interrogation signal, wherein the transceiver is in signal communication with four or more antennae;
   an intraoral image detector that forms an image upon exposure to radiation received from the x-ray source;
   a radio-frequency transponder that is coupled to the image detector and is configured to respond to the interrogation signal by transmitting a wireless response signal;
   a control logic processor that is in communication with the transceiver and that provides an output signal indicative of the spatial position of the image detector according to response signals received from the transponder at the four or more antennae; and
   an indicator that responds to the output signal by indicating the relative position of the image detector.

2. The apparatus of claim 1 wherein the intraoral image detector is taken from the group consisting of a photosensitive film imaging device, a storage phosphor imaging device, and a digital detector device.

3. The apparatus of claim 1 wherein the indicator is a display that further indicates a recommended adjustment of the relative position of the image detector.

4. The apparatus of claim 1 wherein the four or more antennas are encased and disposed at equal distances from each other and from an optical axis of the x-ray source.

5. The apparatus of claim 1 wherein the indicator is coupled to the x-ray source.

6. The apparatus of claim 1 wherein the antennae are planar, in planes that are oblique with respect to an optical axis of the x-ray source.

7. The apparatus of claim 1 wherein the radio frequency transponder is coupled to the center of the image detector.

8. The apparatus of claim 1 wherein the radio-frequency transceiver is in signal communication with four antennae that receive the response signal and a fifth antenna that transmits the interrogation signal.

9. A method for detecting the relative position of an intraoral imaging detector to an x-ray source for obtaining an intraoral x-ray image from a patient, comprising:
   coupling a radio-frequency transceiver to the x-ray source, wherein the transceiver is energizable to transmit an interrogation signal;
   coupling four or more antennae to the radio frequency transceiver, wherein the four or more antennae are spaced at equal intervals about an optical axis of the x-ray source;
   coupling a radio-frequency transponder to the imaging detector, wherein the transponder is configured to respond to the interrogation signal by transmitting a wireless response signal;
   providing an output signal indicative of the spatial position of the image detector according to the response signals received from the transponder at the four or more antennae; and
   responding to the output signal by displaying an indicator indicating the relative position of the image detector.

10. The method of claim 9 wherein the output signal is provided as a result of a triangulation calculation based on relative signal strength at each of the four or more antennae.

11. The apparatus of claim 10 further comprising using received signal strength indicator technology to perform the triangulation calculation.

12. The method of claim 9 wherein displaying the indicator comprises providing a display on a display screen.

13. The method of claim 9 wherein displaying the indicator comprises energizing a guide that is coupled to the x-ray source.

14. The apparatus of claim 9 wherein the intraoral image detector is taken from the group consisting of a photosensitive film imaging device, a storage phosphor imaging device, and a digital detector device.

15. A non-transitory computer-readable medium encoded with a computer software program for detecting the relative position of an intraoral imaging detector with respect to an x-ray source for obtaining an intraoral x-ray image from a patient, such that when the software program is executed on a computer it causes the steps of:
   coupling a radio-frequency transceiver to the x-ray source, wherein the transceiver is energizable to transmit an interrogation signal;
   coupling four or more antennae to the radio frequency transceiver, wherein the four or more antennae are spaced at equal intervals about an optical axis of the x-ray source;
   coupling a radio-frequency transponder to the imaging detector, wherein the transponder is configured to respond to the interrogation signal by transmitting a wireless response signal;
   providing an output signal indicative of the spatial position of the image detector according to the response signals received from the transponder at the four or more antennae; and
   responding to the output signal by displaying an indicator indicating the relative position of the image detector.

* * * * *